United States Patent
Wagner et al.

(10) Patent No.: US 10,076,357 B2
(45) Date of Patent: Sep. 18, 2018

(54) TROCAR SLEEVE WITH AN ASYMMETRICAL HELIX

(71) Applicant: Karl Storz SE & Co. KG, Tuttlingen (DE)

(72) Inventors: Sebastian Wagner, Bretten (DE); Martin Oberlaender, Engen (DE); Alexander Fuchs, Steisslingen (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 0 days.

(21) Appl. No.: 14/881,931

(22) Filed: Oct. 13, 2015

(65) Prior Publication Data

US 2016/0100856 A1  Apr. 14, 2016

(30) Foreign Application Priority Data

Oct. 14, 2014  (DE) .................. 10 2014 114 890

(51) Int. Cl.
*A61M 5/32* (2006.01)
*A61B 17/34* (2006.01)

(52) U.S. Cl.
CPC ...... *A61B 17/3421* (2013.01); *A61B 17/3478* (2013.01); *A61B 17/3474* (2013.01); *A61B 2017/348* (2013.01); *A61B 2017/349* (2013.01); *A61B 2017/3492* (2013.01)

(58) Field of Classification Search
CPC ............ A61B 17/3474; A61B 17/3421; A61B 2017/349; A61B 2017/348; A61B 2017/3492; A61B 17/34; A61B 17/3478; A61B 17/348

USPC .......................................................... 604/175
See application file for complete search history.

(56) References Cited

U.S. PATENT DOCUMENTS

| | | | |
|---|---|---|---|
| 5,630,813 A | 5/1997 | Kieturakis | |
| 5,895,351 A * | 4/1999 | Nottage | A61B 17/3421 600/201 |
| 6,638,265 B1 * | 10/2003 | Ternamian | A61B 17/3421 604/523 |
| 2003/0153926 A1 | 8/2003 | Schmieding et al. | |

(Continued)

FOREIGN PATENT DOCUMENTS

| | | |
|---|---|---|
| DE | 9102553 U1 | 5/1991 |
| DE | 10156312 A1 | 6/2003 |
| EP | 0432363 A2 | 6/1991 |

(Continued)

OTHER PUBLICATIONS

Thomas, Heather Smith, Dealing With Pasture Bloat, Angus Beef Bulletin, Jul. 20, 2012, pp. 1-2.

(Continued)

*Primary Examiner* — Kevin C Sirmons
*Assistant Examiner* — Tiffany Legette-Thompson
(74) *Attorney, Agent, or Firm* — Whitmyer IP Group LLC

(57) ABSTRACT

A trocar sleeve has a hollow shaft having a distal end and a proximal end, the shaft having a rectilinear shaft axis, an external thread rising from an outer surface of the shaft, wherein a first external thread having a shape of a helix has a height, measured from the outer surface up to a vertex of the helix, the height of the helix, seen along the rectilinear shaft axis from distal to proximal increases, and wherein a pitch of the helix, seen along the rectilinear shaft axis from distal to proximal decreases.

25 Claims, 9 Drawing Sheets

(56) References Cited

U.S. PATENT DOCUMENTS

2012/0209205 A1    8/2012  Okihisa et al.

FOREIGN PATENT DOCUMENTS

| EP | 0484725 | A1 | 5/1992 |
| EP | 0484725 | B1 | 3/1996 |
| EP | 2529684 | A2 | 12/2012 |
| EP | 2747678 | B1 | 7/2014 |

OTHER PUBLICATIONS

Extended European Search Report Application No. 15189399.7 completed: Dec. 22, 2015; dated Jan. 8, 2016 5 pages.

* cited by examiner

TROCAR SLEEVE WITH AN ASYMMETRICAL HELIX

FIELD OF THE INVENTION

The invention relates to a trocar sleeve with a hollow shaft which has a distal end and a proximal end and an approximately rectilinear shaft axis, with an external thread rising from the outer face of the shaft.

BACKGROUND OF THE INVENTION

A trocar sleeve of this kind is known from EP 0 484 725 A.

Trocar sleeves are used in minimally invasive procedures to gain access to an internal cavity of the body. In laparoscopy, this is the abdominal cavity. For this purpose, the trocar sleeve has a hollow shaft which, when the trocar sleeve is applied, is placed over an incision in the abdominal wall and pushed through the latter. Thereafter, the distal end of the shaft protrudes into the abdominal cavity, while the proximal end protrudes from the upper face of the abdominal wall In many embodiments, the trocar sleeve is applied by pushing a trocar mandrel into the hollow shaft, said trocar mandrel having a distal tip which extends beyond the distal end of the trocar sleeve. This combination of trocar sleeve and trocar mandrel, i.e. the actual trocar, is pushed through the abdominal wall. Thereafter, the trocar mandrel is withdrawn, such that suitable instruments can then be inserted through the hollow shaft into the body cavity.

In many trocar sleeves, a helically extending external thread is present on and rises from the outer face of the hollow shaft. The trocar sleeve can be screwed in or out through the tissue via this thread.

Particularly in laparoscopy procedures, it is desirable to inflate the internal cavity of the body, i.e. the abdominal cavity, with an insufflation gas in order to provide a better view of the interior. For this purpose, a housing provided with a seal, and with an attachment for delivery of an insufflation gas, is mounted in most cases on the proximal end of the shaft of the trocar sleeve. In many designs, further attachments can be provided on the trocar housing, for example in order to deliver and remove irrigation liquids. In practical use, corresponding hose lines are then attached, as a result of which the trocar sleeve becomes rather top-heavy. This poses the risk of the trocar sleeve changing its position during use, for example by moving in the proximal direction or tilting. It would be fatal if the trocar sleeve were to accidentally slide out of the body during an endoscopy procedure.

In some embodiments, the hollow shaft is made from a flexible material, mostly a plastic material. The clear internal diameter of the hollow shaft defines the maximum diameter of an instrument that can be guided through the trocar sleeve. In many surgical techniques, it is necessary to insert instruments that are curved or are bent sideways. In the case of rigid trocar sleeves, for example those made of steel, such instruments cannot be guided through, or they can be guided through only with deformation. In these cases, flexible trocar sleeves are used. The tubular body of the hollow shaft is made from an elastic polymer that is able to adapt to the bending of the surgical instruments that are passed through. When bent instruments are guided through a trocar sleeve, there is a danger of the latter being shifted.

Moreover, the plastic materials that are used generally have lower coefficients of friction than the materials of rigid trocar sleeves, such that there is additionally the danger of a fitted trocar sleeve shifting.

It is an object of the present invention is to develop a trocar sleeve that can be inserted with minimal trauma into a cavity of the body and that is secured at least against withdrawal from the body.

SUMMARY OF THE INVENTION

According to the invention, the object is achieved by a trocar sleeve, comprising a hollow shaft having a distal end and a proximal end, said shaft having a rectilinear shaft axis, an external thread rising from an outer surface of said shaft, wherein a first external thread having a shape of a helix has a height, measured from said outer surface up to a vertex of said helix, said height of said helix, seen along said rectilinear shaft axis from distal to proximal increases, and wherein a pitch of said helix, seen along said rectilinear shaft axis from distal to proximal decreases.

By virtue of the fact that the height of the helix increases from distal to proximal, the trocar sleeve can be inserted particularly gently by means of rotation and simultaneous penetration of the helix into the tissue. As a result of the gradually increasing height of the helix, the tissue in the area of the incision can be gently spread out further in a gradual manner. By virtue of the simultaneous decrease in the pitch of the helix, a quite considerable axial advance can be achieved per revolution at the start of the rotation. Since the height of the helix is still quite low in this area, this can be done in a particularly atraumatic manner. Although the decreasing pitch means that the advance movement per revolution becomes smaller as the insertion proceeds, this permits gentle widening and a gentle rotation of the helix through a tissue, i.e. an abdominal wall.

When the helix, for example, has been screwed completely through the abdominal wall, the portion of the helix that has the greatest height lies opposite the underside of the abdominal wall. This effectively counteracts a withdrawal of the trocar sleeve by pulling movements of the kind that occur during the manipulation of the trocar housing in a medical procedure. Forces that cause a rotation of the trocar sleeve do not normally occur during such manipulations or medical procedures.

Thus, the trocar sleeve in the area of the helix can be screwed in without any great danger of harming the patient and, after the helix has been screwed through the abdominal wall, it offers considerable resistance to axially directed withdrawal movements.

In further embodiments of the invention, seen from distal to proximal, the angle of the proximal flank of the helix with respect to the shaft axis decreases and approaches approximately 90°.

This measure has the advantage that, after the helix has been screwed through the tissue, a flank lies opposite the underside of the abdominal wall, specifically a flank that extends approximately parallel to the direction of the underside of the abdominal wall, with the result that there is a particularly good blocking action against axial withdrawal in the proximal direction. However, the flank angle in connection with the pitch is still so pronounced that the trocar sleeve can be unscrewed again from the abdominal wall after the medical procedure has been completed. In combination with the maximum height of the helix, a favourably oriented blocking surface is thus available which can come into blocking engagement with the inner face of the tissue of the body cavity.

In a further embodiment of the invention, the height of the helix increases from zero to a maximum height.

This measure has the advantage that the trocar sleeve can initially be placed on the corresponding incision and then advanced linearly until the helix begins to rise. From this point, the trocar sleeve in the area of the helix can be screwed easily and relatively atraumtically through the tissue. The increase from the height zero allows the helix to be screwed particularly gently into the opening in the tissue. The maximum height of the helix depends on the size of the trocar sleeve and also on the nature of the intervention, particularly on which attachments and manipulations take place at the proximal end of the trocar and entail the risk of the trocar being withdrawn in the proximal direction.

In a further embodiment of the invention, the increase in the height of the helix is constant.

This measure has the advantage that the screwing-in can be carried out particularly smoothly, in particular free of jolts.

In a further embodiment of the invention, the maximum height of the helix amounts to the extent of the external diameter of the trocar shaft.

In this height range, the trocar sleeve can be fixed particularly securely against accidental withdrawal.

In a further embodiment of the invention, the height of the helix, following the maximum height, decreases to zero again within at most a 360° winding.

This measure has the advantage that, after the area of maximum height has been screwed through, the trocar sleeve can be screwed in slightly further, such that the tissue behind the screwed-in helix can then immediately bear smoothly on the outer face of the shaft. In other words, no step is present at the end of the helix. This measure also makes it easier to unscrew the trocar sleeve after the medical intervention.

In a further embodiment of the invention, a shaft portion without a thread is present on the distal side of the helix.

This measure has the advantage that this "smooth" portion without external thread can first of all be applied in a "classical" manner and can be driven axially through the tissue in the distal direction. At this point, a trocar mandrel can also already be withdrawn. When the distal end of the helix has reached the outer face of the tissue, the screwing procedure can begin and the trocar sleeve in the area of the helix can be screwed through the tissue, for example the abdominal wall. It is particularly advantageous here that the helix extends over only a portion of the shaft.

In a further embodiment of the invention, a retainer, which is movable along the shaft axis and can be placed on an upper face of a tissue through which the trocar sleeve is pushed, can be arranged on the shaft on the proximal side of the helix.

This measure, which is known per se, can permit improved fixing of the trocar sleeve and, in particular, can additionally prevent the trocar sleeve from accidentally being pushed further in the distal direction.

This securing could in principle also be achieved by a process in which the helix is not screwed completely through the tissue area, i.e. the abdominal wall, and instead threaded portions of the helix with a relatively large height remain in the area of the opening and bear on the underside and also on the upper face. However, this would place an additional strain on the tissue in the area of the opening through which the trocar sleeve is introduced.

It is therefore advantageous to screw the entire helix through the abdominal wall, such that only a smooth, thread-free portion of the shaft remains in the area of the tissue opening. A thread-free portion of this kind is therefore provided on the proximal side of the helix.

In a further embodiment of the invention, the retainer is designed as a disc-like element which is movable along the shaft axis and can be held stationary on the shaft in at least one position.

This measure has the advantage that the holder can be applied and locked in position particularly easily and especially from the outside, i.e. in a way clearly visible to the person handling the trocar sleeve.

In a further embodiment of the invention, the retainer has an internal thread which meshes with a corresponding second external thread on the outer face of the shaft, such that the retainer is movable axially to and fro on the proximal side of the helix.

In a further embodiment of the invention, the retainer is made from a flexible plastic material, and the retainer is movable axially to and fro over a second external thread on the outer face of the shaft.

This measure has the advantage that, on account of the flexible nature of the material, the retainer can easily be pushed with its opening onto the shaft and can be guided axially in the area of the second external thread. The internal thread in the opening of the retainer can be omitted for manufacturing reasons. A retainer of such configuration can also be pushed onto a shaft without a second external thread and can be moved along same. The opening in the retainer is then of such a dimension that it is slightly widened by the shaft, and the retainer sits on the shaft with a frictional fit and can be moved when the frictional force is overcome.

The retainer can also be designed as a slit or U-shaped element that can be clipped laterally onto the shaft.

It is advantageous to provide a thread-free shaft portion in the area between the helix and the second external thread. The tissue can bear gently on this smooth area of the outer face of the shaft. In the slit design of the retainer, the latter can be clipped on laterally in this area.

It will be appreciated that the aforementioned features and the features still to be explained below can be used not only in the cited combinations but also in other combinations, without departing from the scope of the present invention.

BRIEF DESCRIPTION OF THE DRAWINGS

The invention is described and explained in more detail below with reference to the attached drawings, in which.

DETAILED DESCRIPTION OF THE INVENTION

A trocar sleeve shown in the figures is designated in its entirety by reference number 10.

Figure 1:
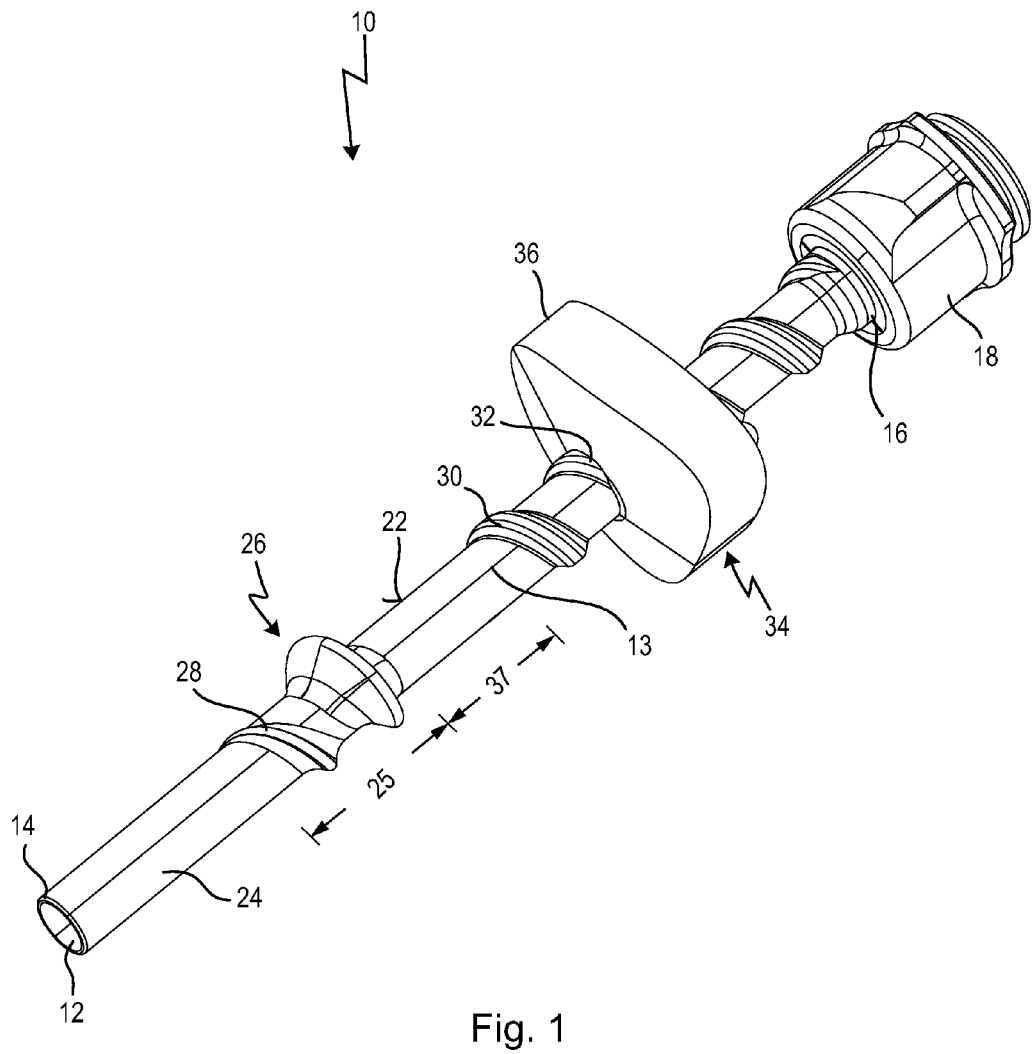
FIG. 1 shows a perspective view of a trocar sleeve according to the invention without a proximal seal.
Figure 2:
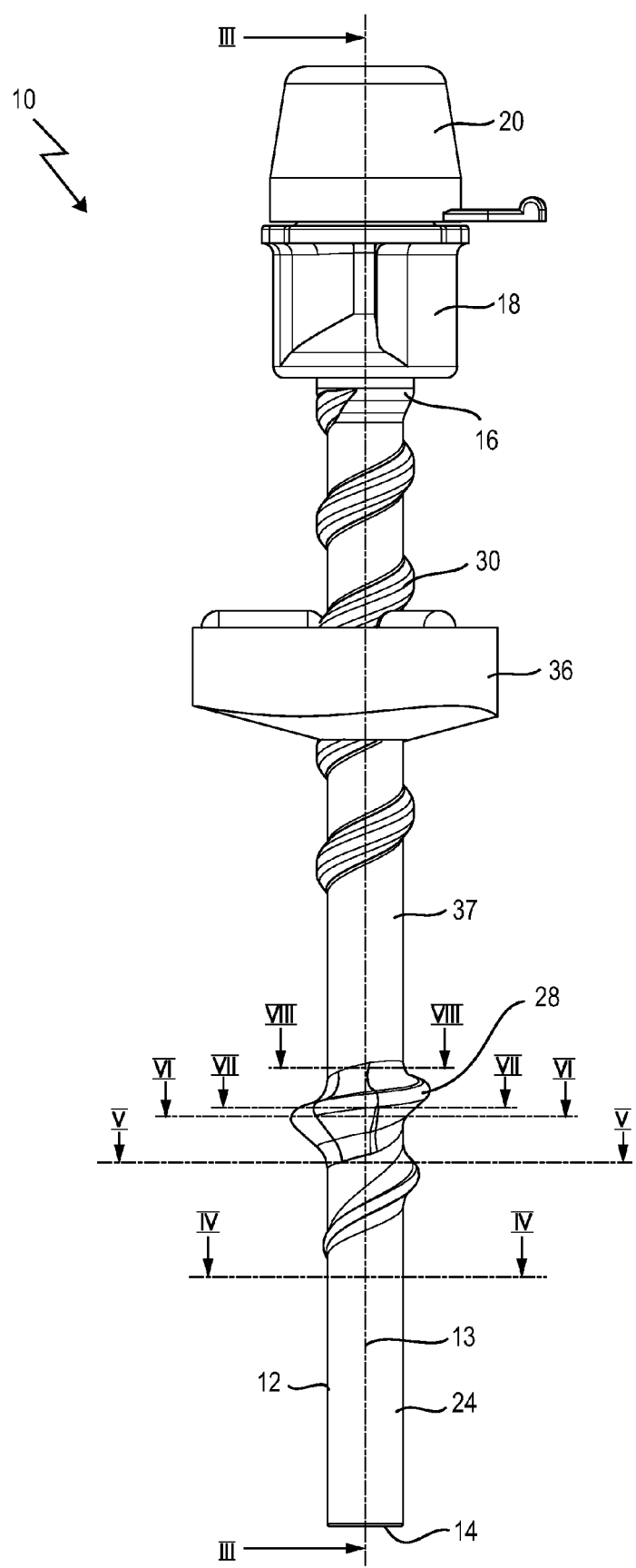
FIG. 2 shows a side view of the trocar sleeve with a proximal seal.

As can be seen in particular from FIGS. 1 and 2, the trocar sleeve 10 has a rectilinearly extending hollow shaft 12, which has a shaft axis 13. The shaft 12 is cylindrical and has a cylindrical outer face 22.

The shaft 12 has an open distal end 14 and is provided, at its proximal end, with a housing 18 that can be closed in a gas-tight manner by a seal 20 (FIG. 2). As can be seen from FIGS. 1 and 2, the outer face 22 is smooth in a distal end portion 24 of the shaft 12, i.e. has no thread there.

This distal end portion 24 is adjoined in the proximal direction by a longitudinal portion 25 on which a first external thread 26 is present in the form of a helix 28, wherein the helix 28 rises from the cylindrical outer face 22 of the shaft 12.

The exact design of the helix 28 will first be described and explained in detail in particular in connection with FIG. 2 and with the sectional views in FIGS. 3 to 8.

In the illustrative embodiment shown, the helix 28 is constructed from a helical winding which has approximately two complete thread turns.

Figure 2A:
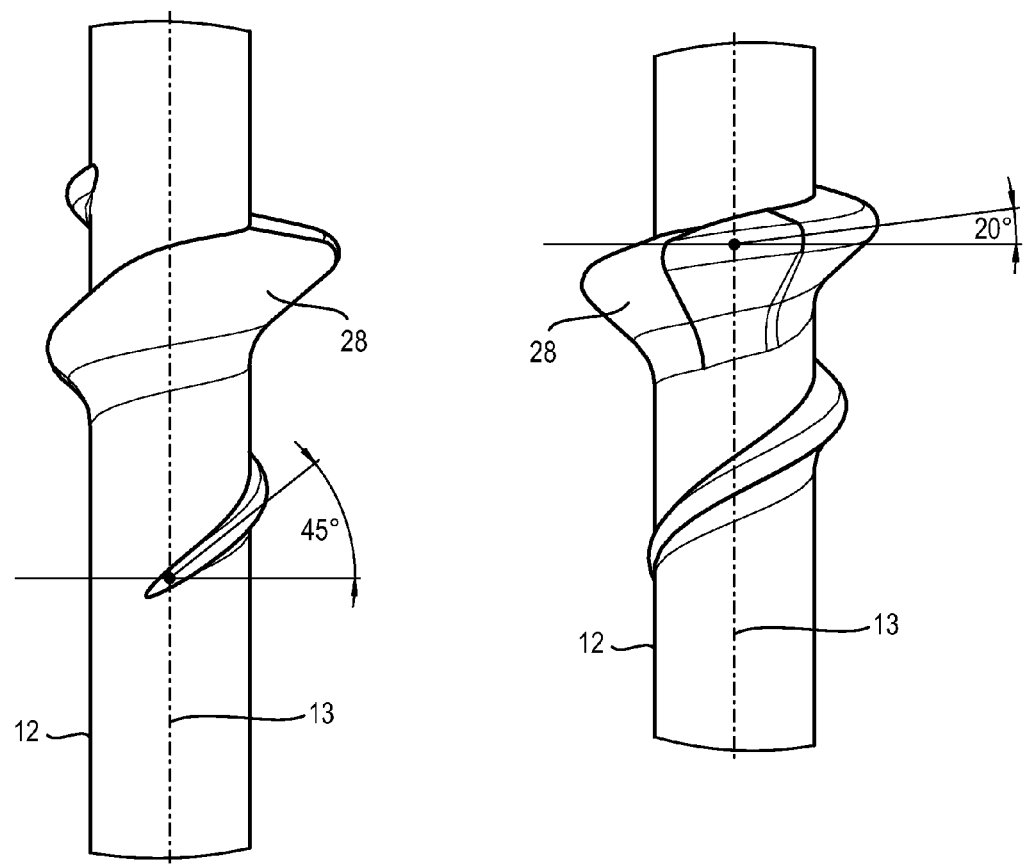
FIG. 2a shows a side view of the trocar sleeve with demonstrating an angle of gradient of the helix.

As can be seen from FIG. 2a, the helix 28 and the respective vertex line of the first outer thread has an angle of gradient with respect to a plane perpendicular to the shaft axis 13, which changes, seen from distal to proximal, from an acute angle of more than 45 degrees to an angle of less than 20 degrees. The vertex line is the line where all vertices of the helix lie.

Figure 3:
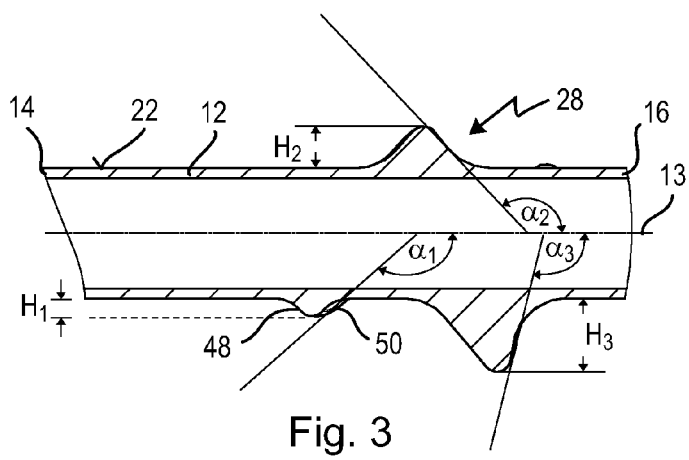
FIG. 3 shows a longitudinal section along the line III-III in FIG. 2 in the area of the helix.
Figure 4:
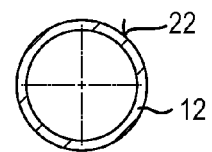
FIG. 4 shows a cross section along the line IV-IV in FIG. 2.

It will be seen from the sectional views in FIGS. 3 and 4 that, viewed from the distal end 14 in the direction of the proximal end 16, the helix 28 rises from a height zero through a height H1 and a height H2 to a maximum height H3. The increase is constant.

Figure 5:
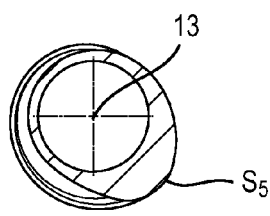
FIG. 5 shows a cross section along the line V-V in FIG. 2.
Figure 6:
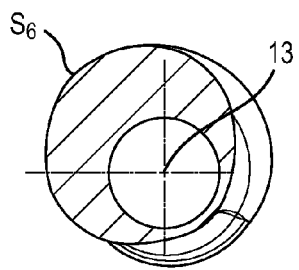
FIG. 6 shows a cross section along the line VI-VI in FIG. 2.
Figure 7:
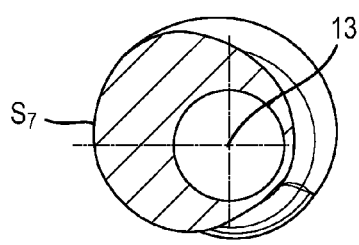
FIG. 7 shows a cross section along the line VII-VII in FIG. 2.
Figure 8:
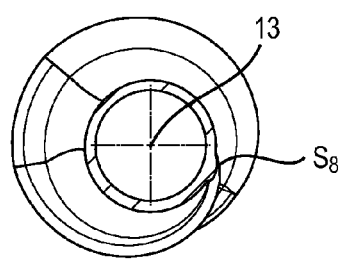
FIG. 8 shows a cross section along the line VIII-VIII in FIG. 2.

The helix begins at a height zero, then immediately rises to a height of approximately 2.7 mm, has a height of 5 mm in the area of the cross section in FIG. 5, and it has a height of 6.5 mm at the level of the cross sections in FIGS. 6 and 7. Following the maximum height H3 of approximately 6.5 mm, the height drops very rapidly again (ca. 90°) to a very low height of approximately 2.7 mm, as is shown in FIG. 8.

The respective heights are indicated in FIGS. 5 to 8 by the vertices S5, S6, S7 and S8.

Turning now to FIG. 2, it will be seen that the pitch of the helix decreases continuously from distal to proximal. The pitch is defined by the height difference of two opposite vertices after a 360° rotation.

The pitch at the start of the helix 28, i.e. according to the cross section in FIG. 4, is 20 mm per revolution, the pitch in the area of the cross section in FIG. 5 is in the range of 10 mm per revolution, the pitch in the area of the cross section in FIG. 6 is in the range of 7 mm per revolution, and the pitch in the area of the cross section in FIG. 7 is only 4 mm per revolution. Following the maximum, the pitch is 8 mm per revolution.

The term "per revolution" is to be understood as meaning that, if one takes this point and if one were to make a complete revolution, this pitch would result.

In actual fact, however, the pitch of the helix 28 changes continuously from distal to proximal.

It will be seen in particular from the sectional view in FIG. 3 that the angle of the distal flank 48 of the helix 28 remains almost unchanged.

However, the angle of the flank 50 directed towards the proximal end decreases continuously. The flank angle α of the flank 50 is the angle between the flank 50 and, seen from distal to proximal, the shaft axis 13. Thus, at the start of the helix, the flank angle $\alpha_1$ with respect to the shaft axis 13, seen from distal to proximal, is approximately 140°. This flank angle decreases such that, for example, the flank angle $\alpha_2$ is approximately 130°. In the area of the last winding, i.e. in the area of the maximum height $H_3$, the flank angle $\alpha_3$ is not quite 100°.

Overall, the height H of the helix 28 in the shaft portion 25 thus increases from zero to the maximum height $H_3$ and then drops rapidly. The whole thread turn of the helix 28 includes approximately two complete 360° revolutions.

At the same time, the pitch decreases, seen from distal to proximal, and the angle of the flank of the helix with respect to the shaft axis 13, directed towards the proximal end, becomes ever smaller.

Returning to FIGS. 1 and 2, it will first be noted that the shaft portion 25 with the helix 28 is adjoined by a thread-free portion 37. Following this thread-free portion 37, a second external thread 30 rises from the outer face 22 of the shaft, but this second external thread is configured as a "regular" external thread with a constant height, constant pitch and constant flank shape.

A retainer 34 in the form of a triangular disc 36 is received on this second external thread 30. The retainer 34 is made from a flexible silicone material. The triangular disc 36 can be moved axially in the proximal or distal direction. The triangular shape makes it easier to grip and turn or move the retainer. In the area of its central opening 32, the flexible silicone material bears, as as result of deformation, on the contour of the second external thread 30.

An example of a use of the trocar sleeve 10 according to the invention in laparoscopy will be described with reference to the sequence of FIGS. 9 to 13.

Figure 9:
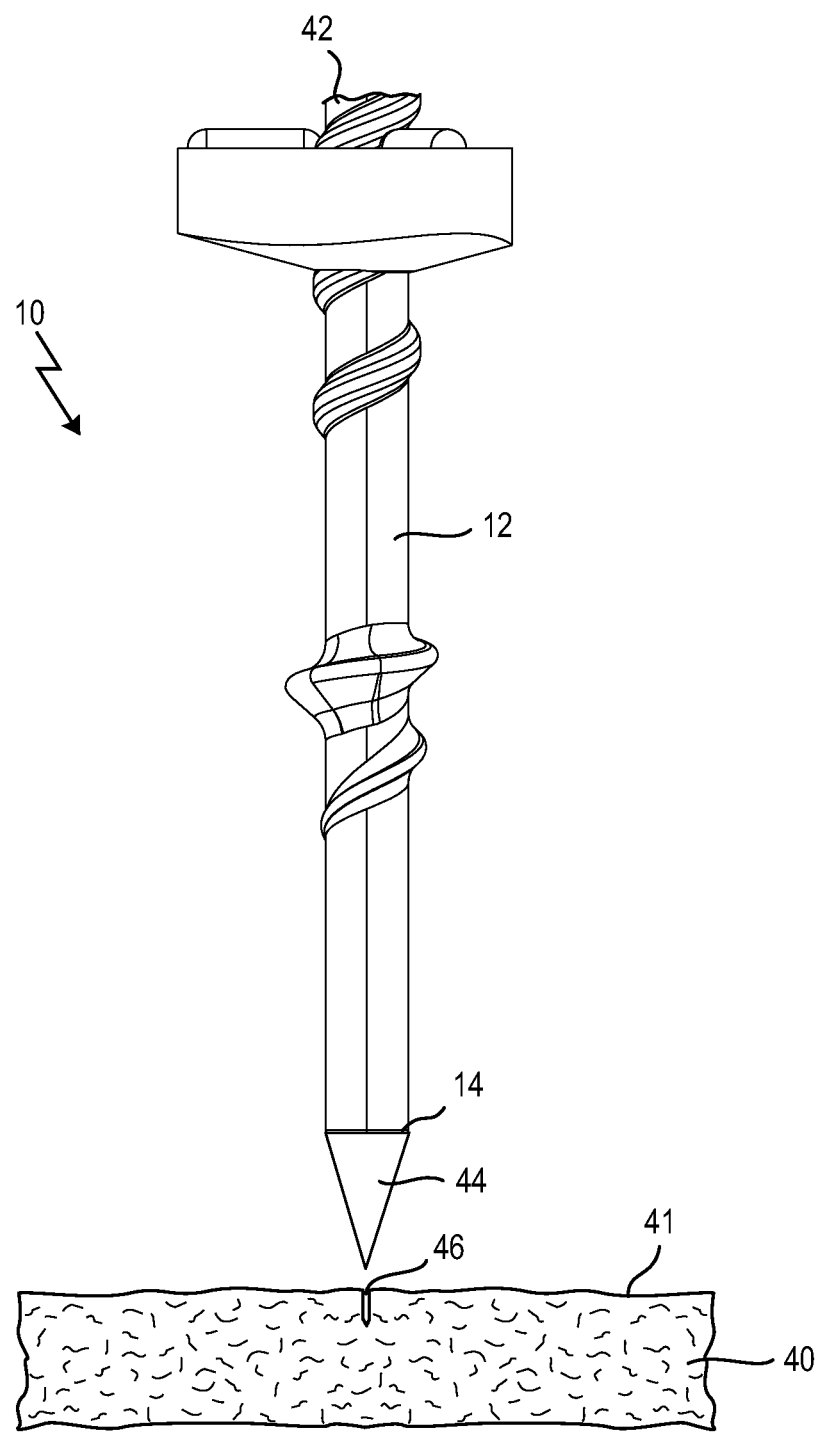
FIG. 9 shows a partial side view of the trocar sleeve with a trocar mandrel pushed in shortly before placement on an abdominal wall.
Figure 10:
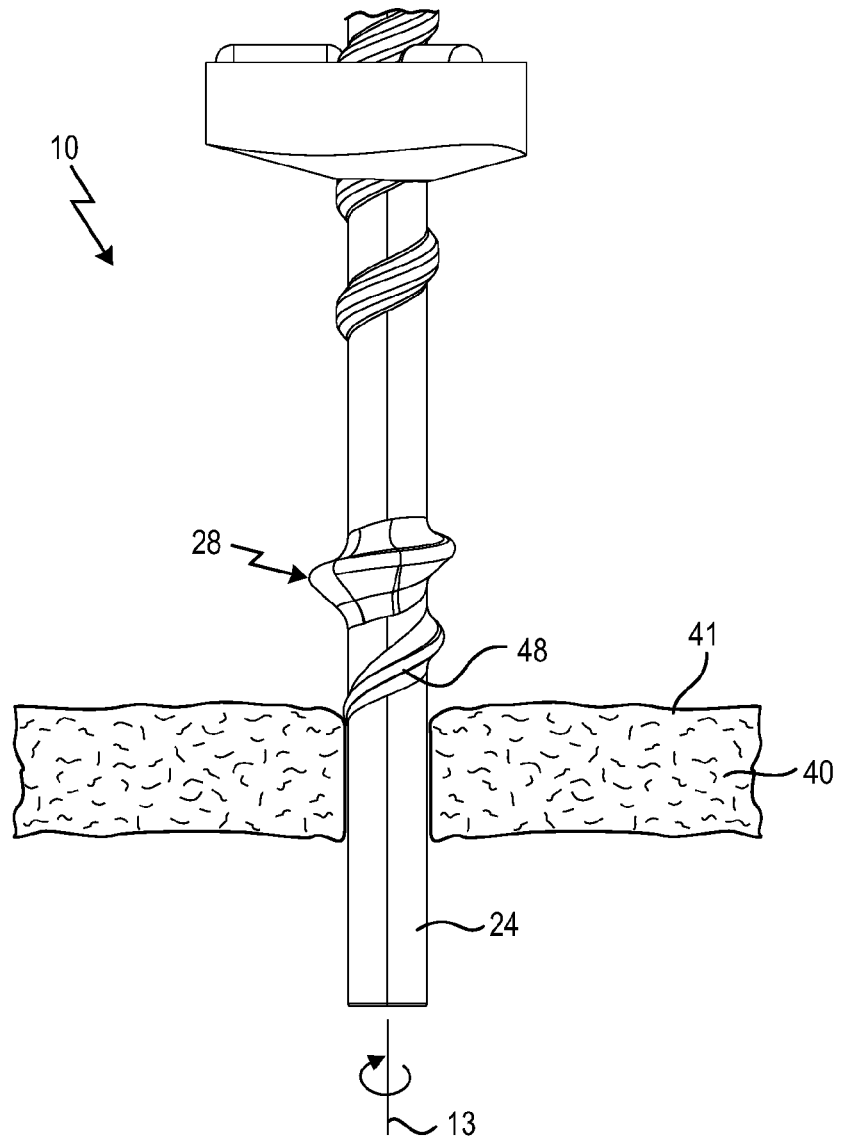
FIG. 10 shows a view corresponding to FIG. 9, in a situation in which a distal end portion of the shaft has already been pushed through the abdominal wall and the trocar has been withdrawn.

As can be seen from FIG. 9, a trocar mandrel 42 is pushed into the inner space of the shaft 12 and its tip 44 extends past the distal end of the trocar sleeve 10. This tip 44 is placed on an incision 46 on the upper or outer face 41 of an abdominal wall 40. When this assembly is pushed forward axially, the trocar sleeve 10 is initially pushed via the smooth distal end portion 24 through the abdominal wall 40, until the helix 28 reaches the upper face 41, as is shown in FIG. 10. The trocar mandrel 42 can now be withdrawn.

Figure 11:
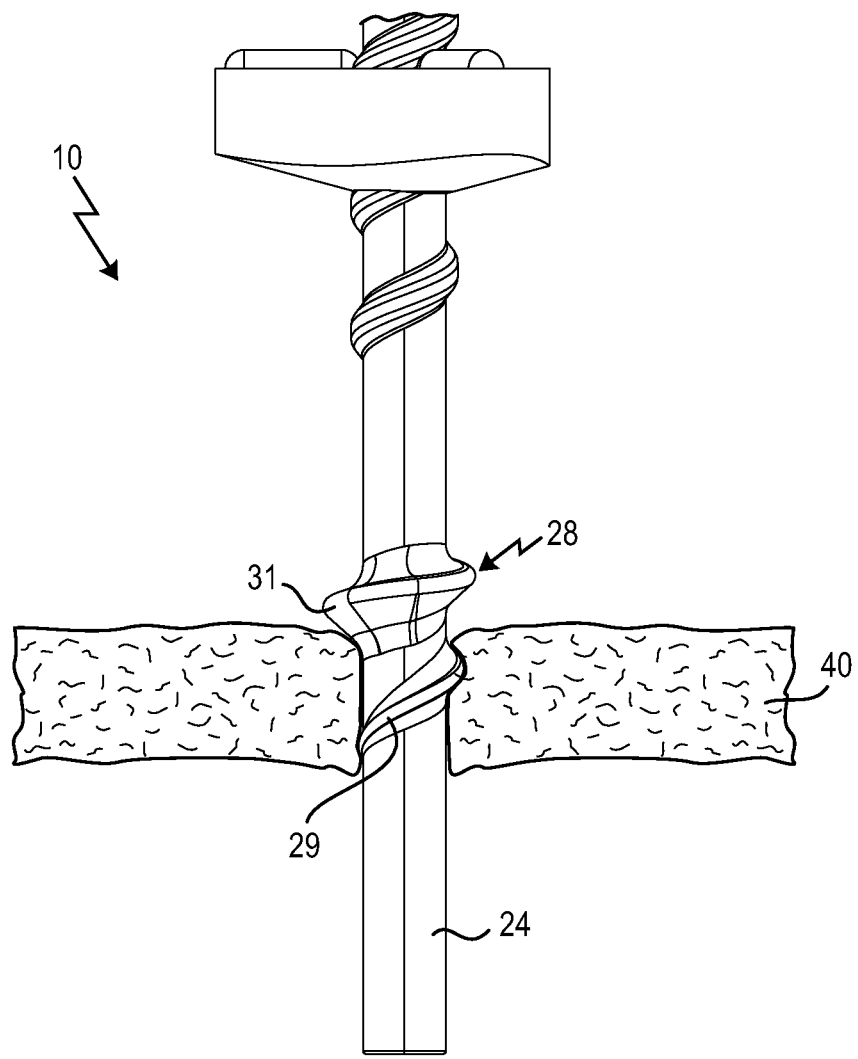
FIG. 11 shows a situation comparable to FIG. 10 as the helix begins to be screwed into the abdominal wall.

As can be seen from the transition from FIG. 10 to FIG. 11, the helix 28 is now screwed gradually through the abdominal wall 40. It is therefore the area of the helix 28 provided with the low height but with the high pitch that is first to enter the abdominal wall. The trocar sleeve 10 can thus be screwed in by a certain distance through a 360° revolution, as can be seen from the transition from FIG. 10 to FIG. 11.

Figure 12:
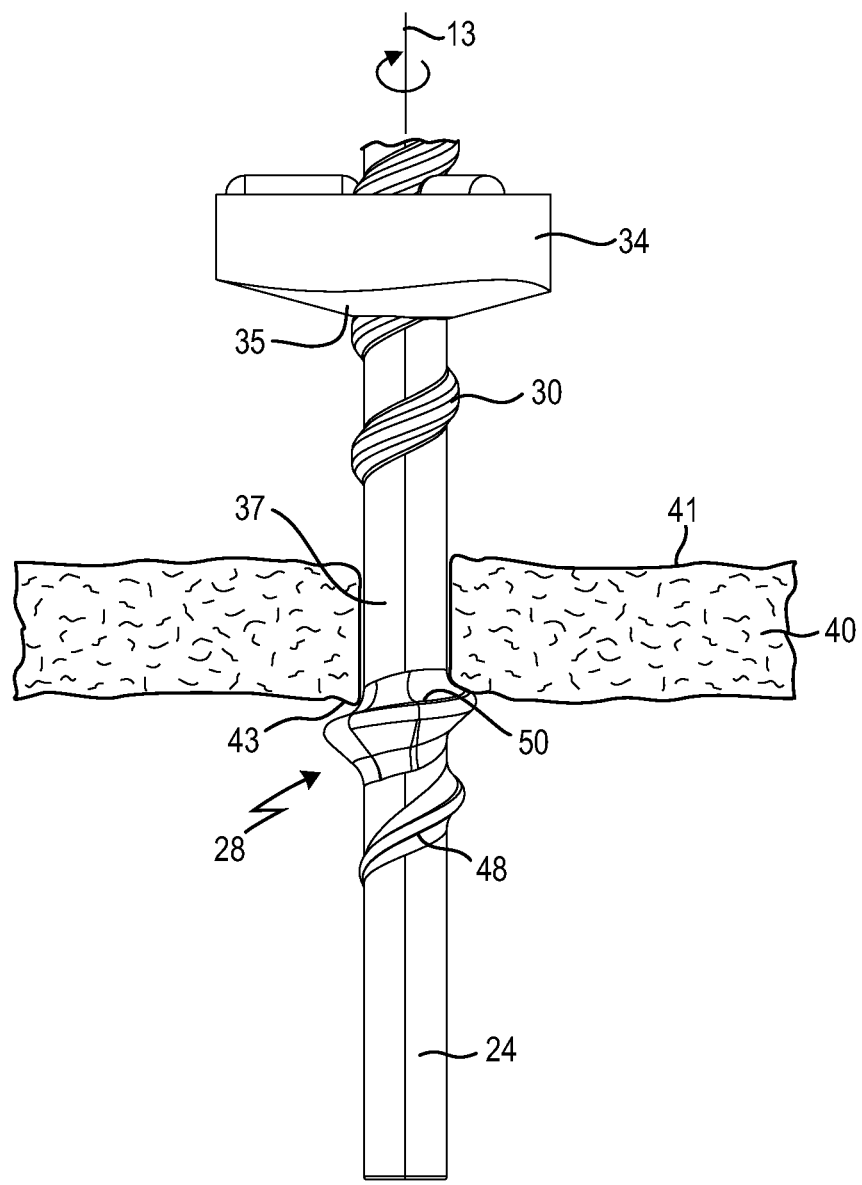
FIG. 12 shows a situation in which the helix has been screwed completely through the abdominal wall.

By further rotation of the trocar sleeve 10 about the shaft axis 13, the helix 28 is screwed in further and all the way through the abdominal wall 40. This is shown in FIG. 12. It is clear that at least one further 360° revolution was necessary for this. The first outer thread 26 has only two complete windings. The overall pitch of the two windings approximately corresponds to the height of the tissue, i.e. the abdominal wall 40 through which the trocar sleeve 10 has to be turned.

From FIG. 11 it can be seen that in the direction of the axis relatively large surface areas between the windings 29 and 31 are present, onto which free space, the tissue of the abdominal wall can rest. Less tissue has to be dilated resulting in less stress and turning through of the helix 28 needs less force. Additionally, less torsional stresses act on the shaft during turning. This opens to produce the shaft from a flexible plastic material. This also opens the possibility to form the shaft together with the helix with a blow-mold procedure.

The proximal flank 50 with the small inclination angle $\alpha_3$ (see FIG. 3) now lies opposite the underside 43 of the abdominal wall 40. At the same time, the height H of the helix 28 is at its most pronounced in this area. It is thus clear from FIG. 12 that the helix 28 offers considerable resistance to an axial movement of the trocar sleeve 10 in the proximal direction.

This prevents a situation in which, during the usual manipulations, the trocar sleeve 10 is inadvertently withdrawn from the abdominal wall 40.

Figure 13:
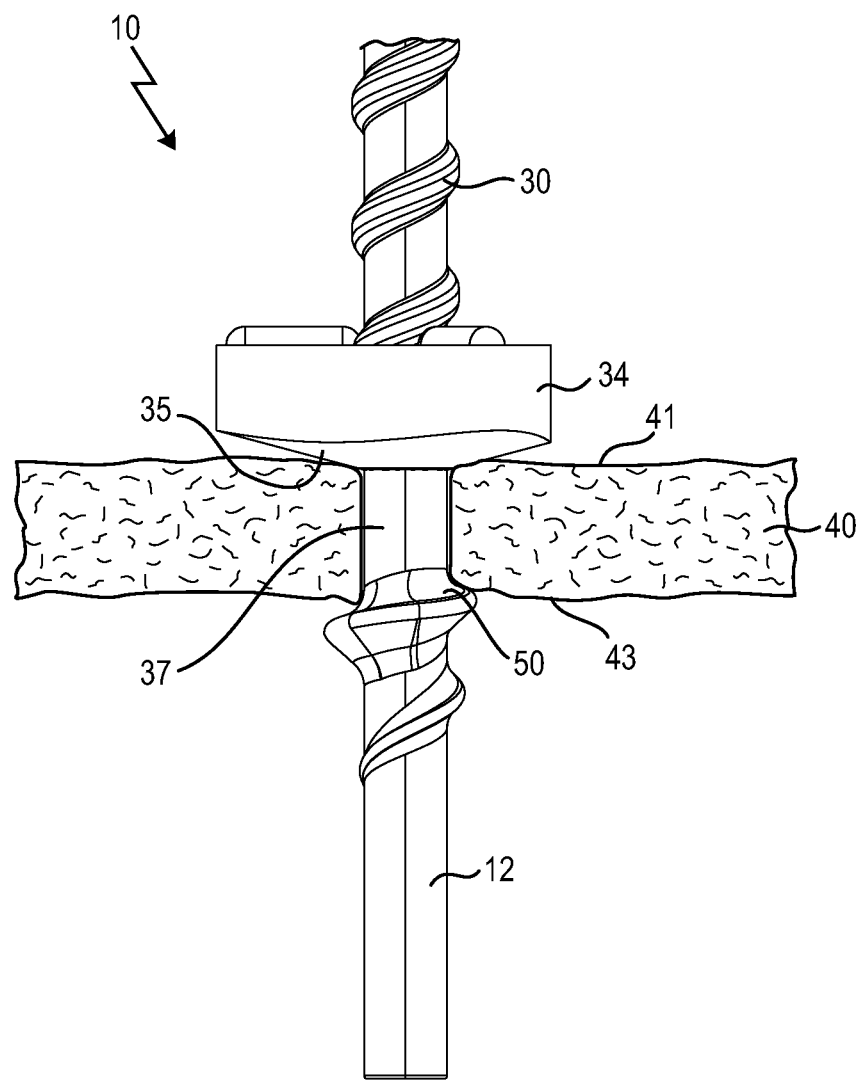
FIG. 13 shows a situation in which a retainer is placed onto the outer face of the abdominal wall.

The retainer 34 is provided as an additional safety feature, it being possible for the retainer 34 to be rotated about the second external thread 30 until its underside comes to lie on the upper face 41 of the abdominal wall 40, as is shown in FIG. 13.

In this position, the trocar sleeve 10 is secured against axial movement both in the proximal direction and also in the distal direction and is also held relatively stable against tilting. It will be seen from FIG. 13 that the tissue in the area of the opening in the abdominal wall 40 has positioned itself around the thread-free, smooth portion 37 between the end of the helix 28 and the start of the second external thread 30. That is to say, the tissue is not adversely affected by the two external threads 26 and 30, not even during protracted interventions.

After completion of the surgical procedure, the trocar sleeve 10 is unscrewed again from the abdominal wall 40, this being made easier by the fact that the helix 28 is continued proximally of the maximum elevation to the height zero but with a small pitch.

What is claimed is:

1. A trocar sleeve, comprising:
   a hollow shaft having a distal end and a proximal end, said shaft having a rectilinear shaft axis; and
   an external thread rising from an outer surface of said shaft, said external thread comprising a first external thread having a shape of a helix has a height, measured from said outer surface up to a vertex of said helix;
   wherein said height of said helix is non-constant and increases gradually in a direction extending along said rectilinear shaft axis from said distal end toward said proximal end;
   wherein a pitch of said helix is non-constant and decreases gradually in a direction extending along said rectilinear shaft axis from said distal end toward said proximal end;
   wherein said helix has a distal flank and a proximal flank; and
   wherein an angle of said proximal flank with respect to said rectilinear shaft axis is non-constant and decreases gradually in a direction extending along said rectilinear shaft axis from said distal end toward said proximal end, said angle defined between said proximal flank and said rectilinear shaft axis in a plane in which said rectilinear shaft axis extends.

2. The trocar sleeve of claim 1, wherein said angle of said proximal flank decreases up to approximately 90 degrees.

3. The trocar sleeve of claim 1, wherein said height of said helix increases constantly.

4. The trocar sleeve of claim 1, wherein an angle of gradient of said pitch of said helix, with respect to a plane extending perpendicular to said rectilinear shaft axis and in a direction extending along said rectilinear shaft axis from said proximal end toward said distal end, changes from an acute angle of more than 45 degrees to an angle of less than 20 degrees.

5. The trocar sleeve of claim 1, wherein said pitch of said helix amounts approximately half of a thickness of a tissue through which said trocar sleeve has to be turned in.

6. The trocar sleeve of claim 1, wherein said helix extends about two windings of said thread.

7. The trocar sleeve of claim 1, wherein distally to said helix a distal portion of said outside of said shaft is present without a thread.

8. The trocar sleeve of claim 1, wherein said helix extends over one section of said shaft only.

9. The trocar sleeve of claim 1, wherein said hollow shaft is cylindrical.

10. The trocar sleeve of claim 1, wherein said hollow shaft and said first external thread are integrally shaped.

11. The trocar sleeve of claim 1, wherein said height of said helix is non-constant and increases gradually in said direction extending along said rectilinear shaft axis, such that such that said height has a first height magnitude at a distal position along said helix, and said height has a second height magnitude at a proximal position along said helix, said first height magnitude being less than said second height magnitude;
   wherein a pitch of said helix is non-constant and decreases gradually in said direction extending, such that said pitch has a first pitch magnitude at a distal position along said helix, and said pitch has a second pitch magnitude at a proximal position along said helix, said first pitch magnitude being greater than said second pitch magnitude; and
   wherein said angle of said proximal flank with respect to said rectilinear shaft axis is non-constant and decreases gradually in said direction extending along said rectilinear shaft axis, such that said angle has a first angle magnitude at a distal position along said helix, and said angle has a second angle magnitude at a proximal position along said helix, said first angle magnitude being greater than said second angle magnitude.

12. The trocar sleeve of claim 1, wherein said height of said helix increases from zero to a maximum height.

13. The trocar sleeve of claim 12, wherein said maximum height amounts up to an external diameter of said shaft.

14. The trocar sleeve of claim 1, wherein said height of said helix increases from zero to a maximum height, and wherein said height, following to said maximum height, decreases to zero.

15. The trocar sleeve of claim 14, wherein said height following to said maximum height, decreases to zero within at most one 360 degree winding of said helix.

16. The trocar sleeve of claim 1, wherein said shaft is made from a flexible material.

17. The trocar sleeve of claim 16, wherein said flexible material is a plastic material.

18. The trocar sleeve of claim 1, wherein a retainer is arranged on said outside of said shaft proximal to said helix, wherein said retainer is movable along said rectilinear shaft axis and arranged to be placed on an outer surface of a tissue through which the trocar sleeve has to be turned through.

19. The trocar sleeve of claim 18, wherein said retainer is designed as a slit element that is arranged to be clipped laterally onto said shaft.

20. The trocar sleeve of claim 18, wherein said retainer is designed as a disc-like element which is movable along said rectilinear shaft axis and which retainer is held stationary on said shaft in at least one position.

21. The trocar sleeve of claim 18, wherein said retainer is made from a flexible plastic material, and wherein said retainer is movable axially to and fro over a second external thread on said outer surface of said shaft.

22. The trocar sleeve of claim 18, wherein said retainer has an internal thread, and wherein said outer surface of said shaft is provided with a second external thread on a side proximal to said helix, said retainer is arranged to be axially moved to and fro over said second external thread.

23. The trocar sleeve of claim 22, wherein a thread-free shaft portion is present between said helix and said second external thread.

24. A trocar sleeve, comprising:
   a shaft having a rectilinear shaft axis extending between a distal end and a proximal end of the shaft, the shaft being hollow; and
   an external thread rising from an outer surface of the shaft, the external thread being helically-shaped and having a distal flank, a proximal flank, and a vertex where the distal flank and the proximal flank meet, and the external thread having a height defined between the outer surface of the shaft and the vertex of the external thread;
   wherein the height of the external thread is non-constant and increases in a direction extending along the rectilinear shaft axis from the distal end toward the proximal end, such that the height has a first height magnitude at a distal position along the external thread, and the height has a second height magnitude at a proximal position along the external thread, the first height magnitude being less than the second height magnitude;
   wherein a pitch of the external thread is non-constant and decreases in a direction extending along the rectilinear shaft axis from the distal end toward the proximal end, such that the pitch has a first pitch magnitude at a distal position along the external thread, and the pitch has a second pitch magnitude at a proximal position along the external thread, the first pitch magnitude being greater than the second pitch magnitude; and
   wherein an angle is defined between the proximal flank and the rectilinear shaft axis in a plane in which the rectilinear shaft axis extends, and the angle is non-constant and decreases in a direction extending along the rectilinear shaft axis from the distal end toward the proximal end, such that the angle has a first angle magnitude at a distal position along the external thread, and the angle has a second angle magnitude at a proximal position along the external thread, the first angle magnitude being greater than the second angle magnitude.

25. The trocar sleeve of claim 24, wherein the height of the external thread increases gradually in the direction extending along the rectilinear shaft axis from the distal end toward the proximal end;
   wherein the pitch of the external thread decreases gradually in the direction extending along the rectilinear shaft axis from the distal end toward the proximal end; and
   wherein the angle is non-constant and decreases gradually in the direction extending along the rectilinear shaft axis from the distal end toward the proximal end.

* * * * *